United States Patent [19]
Rorabaugh

[11] Patent Number: 6,116,738
[45] Date of Patent: Sep. 12, 2000

[54] CORNEAL TOPOGRAPHER WITH CENTRAL AND PERIPHERAL MEASUREMENT CAPABILITY

[75] Inventor: Dale A. Rorabaugh, Rancho Sante Fe, Calif.

[73] Assignee: Vismed, Inc., San Diego, Calif.

[21] Appl. No.: 09/002,549

[22] Filed: Jan. 2, 1998

Related U.S. Application Data

[60] Provisional application No. 60/034,759, Jan. 6, 1997.

[51] Int. Cl.[7] ........................................ A61B 3/00
[52] U.S. Cl. .......................................... 351/247; 351/212
[58] Field of Search ................................. 351/212, 247, 351/211, 246, 205, 200

[56] References Cited

U.S. PATENT DOCUMENTS

| | | | |
|---|---|---|---|
| 3,542,458 | 11/1970 | Volk | 351/39 |
| 4,420,228 | 12/1983 | Humphrey . | |
| 4,692,003 | 9/1987 | Adachi et al. . | |
| 4,863,260 | 9/1989 | Gersten et al. | 351/212 |
| 4,978,213 | 12/1990 | El Hage | 351/212 |
| 5,054,907 | 10/1991 | Sklar et al. . | |
| 5,110,200 | 5/1992 | Snook | 351/212 |
| 5,227,818 | 7/1993 | El Hage | 351/212 |
| 5,283,598 | 2/1994 | McMillam et al. | 351/212 |
| 5,526,172 | 6/1996 | El Hage | 351/208 |
| 5,585,572 | 12/1996 | Kohayakawa | 351/212 |
| 5,587,748 | 12/1996 | Luce et al. | 351/208 |

FOREIGN PATENT DOCUMENTS

WO 96/13199  5/1996  WIPO .

*Primary Examiner*—Hung Xuan Dang
*Attorney, Agent, or Firm*—Fleshner & Kim

[57] ABSTRACT

A videokeratograph has a placido disc with rings concentric about a central axis, a center positioned on the central axis, and an observation opening at the center. A plurality of fixation points are positioned in the placido disc spaced from the center opening and distributed circumferentially around the central axis, whereby rings on the placido disc spaced from the center are reflected from the central zone of the cornea. A video camera positioned on the center axis behind the placido disc observes an image of the placido disc reflected from the cornea. A processor coupled to the video camera determines the shape of the central zone of the cornea.

24 Claims, 2 Drawing Sheets

CORNEAL TOPOGRAPHER WITH CENTRAL AND PERIPHERAL MEASUREMENT CAPABILITY

CROSS-REFERENCE TO RELATED APPLICATIONS

This application claims the benefit of U.S. Provisional application Ser. No. 60/034,759, filed Jan. 6, 1997.

BACKGROUND OF THE INVENTION

1. Field of the Invention

The present invention relates to the field of corneal topographers, and particularly to corneal topographers determining cornea topography from an image of a placido disc reflected from an eye and observed through the center of the disc.

2. Description of Related Art

Corneal topographers are instruments that measure the anterior surface of the cornea. The most commonly used topographer is the videokeratograph, which is based on what is known as a placido disc design. A placido disc consists of a series of concentric circles of alternating black and white rings or other colors. Originally, the placido disc rings were positioned in a flat plane, but now the rings usually have a three dimensional configuration. The disc is illuminated, typically from the rear and placed in front of the cornea to be measured.

A reflection of the rings is obtained from the corneal surface when observed, such as by viewing, photographing or videographing the corneal image through a hole in the center of the disc. A principal deficiency of this method is that the central hole through which the target reflection is measured contains no object that is reflected from the central cornea, and hence this corneal area cannot be measured. Additionally, areas immediately adjacent to the central cornea also cannot be measured because the distance is too small to provide a reliable measurement based upon the optical laws of object-to-image relationships. There is therefore a need for a method of accurately measuring the central zone of a cornea using a placido disc based corneal topographer. As used herein, the central zone of the cornea is a region containing the entrance pupil.

SUMMARY OF THE INVENTION

The present invention provides a method and apparatus for accurately measuring the topography of the central zone of a cornea, as well as other regions of the cornea, using a placido disc based corneal topographer. In the method of the invention this is provided by (a) positioning an eye on a central axis; (b) illuminating the eye through a placido disc having a center and a center opening at the center, the center being on the central axis and the disc having rings concentric about the central axis; (c) fixating the eye along a first viewing axis to a first fixation point positioned in the placido disc spaced from the center opening; (d) observing an image of the placido disc reflected from the eye along the central axis, whereby the central zone of the cornea of the eye reflects images of rings on the placido disc spaced from the center; and (e) determining from the observed image of the cornea the shape of at least the central zone of the cornea.

The preferred method of the invention further includes sequentially fixating the eye to a plurality of fixation points spaced radially from the central axis and circumferentially around the placido disc. At each fixation point, an image of the placido disc is reflected from a different region of the cornea. Accordingly, the shape of at least the central zone of the cornea from each observed image is then determined.

In an apparatus according to the present invention, a placido disc has rings concentric about a central axis, a center positioned on the central axis, and a center opening at the center. At least a first fixation point is positioned in the placido disc spaced from the center opening, whereby the central zone of the cornea of an eye fixated on the fixation point reflects images of rings on the placido disc spaced from the center. A means is positioned on the center axis for observing through the center opening an image of the placido disc reflected from the cornea of an eye positioned at an observation station. Finally, a means is coupled to the observing means for determining the shape of at least the central zone of the cornea from the observed image. The preferred embodiment of the invention includes a plurality of fixation points distributed around the center of the placido disc.

A particularly advantageous feature of this invention is that the central zone of the cornea is positioned on peripheral rings of the placido disc image. Accurate measurements of the central zone of the cornea are thereby made, whereas it is impossible to measure the corneal apex when the fixation point is on the central axis, as is conventional. Further, the off-axis fixation point provides imaging of a radially larger area of the cornea, and the entire cornea is measured by compiling a plurality of measurements taken when a plurality of fixation points distributed around the central axis are used. These and other features and advantages of the present invention will be apparent from the preferred embodiment described in the following detailed description and illustrated in the accompanying drawings.

DETAILED DESCRIPTION OF THE PREFERRED EMBODIMENT(S)

Figure 1:
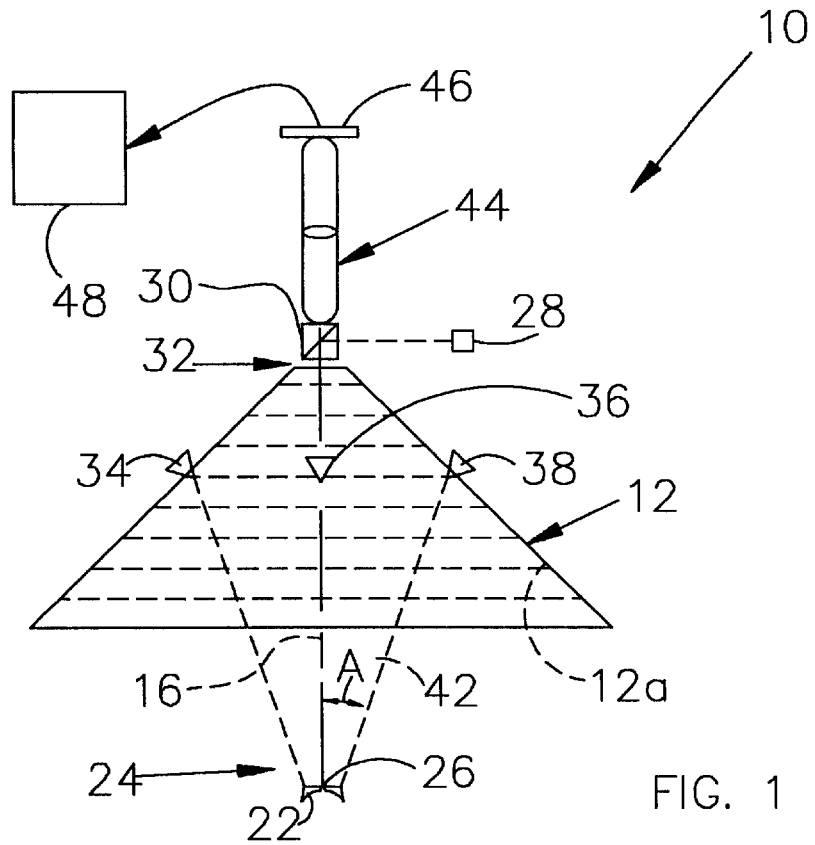
FIG. 1 is a simplified top plan view of a corneal topographer with a placido disc made according to the invention.

As has been mentioned, the invention provides a method and apparatus for accurately measuring the central zone of a cornea using a placido disc based corneal topographer. A videokeratograph made according to the invention is shown generally at 10 in FIG. 1. Videokeratograph 10 includes a conventional placido disc 12 shown formed as a cone having an inside surface 12a with rings 14 concentric about a central axis 16. The rings have alternating contrasting colors, such as black rings 18, represented by the dashed lines, and white rings 20. Disc 12 is typically backlit, but other forms of creating the alternating ring light source may be used, all of which are included in the common term placido disc.

A person's head is located to position an eye 22 to be observed at an observation station 24 with the cornea 26 of the eye located on central axis 16. A videokeratograph typically has a fixation point 28, such as an LED light source. This fixation point is aligned with the central axis with a conventional beam splitter 30 and viewable through a hole 32 in the center of the disc. Videokeratograph 10 however has a plurality of fixation points 34, 36, 38, 40 positioned to be visible to eye 22 and located at 90° intervals in one of the disc rings, as shown. When eye 22 is fixated on a fixation point along what is referred to as a viewing axis 42, the viewing axis is usually at an angle A of 5° to 20° to central axis 16.

Figure 3:
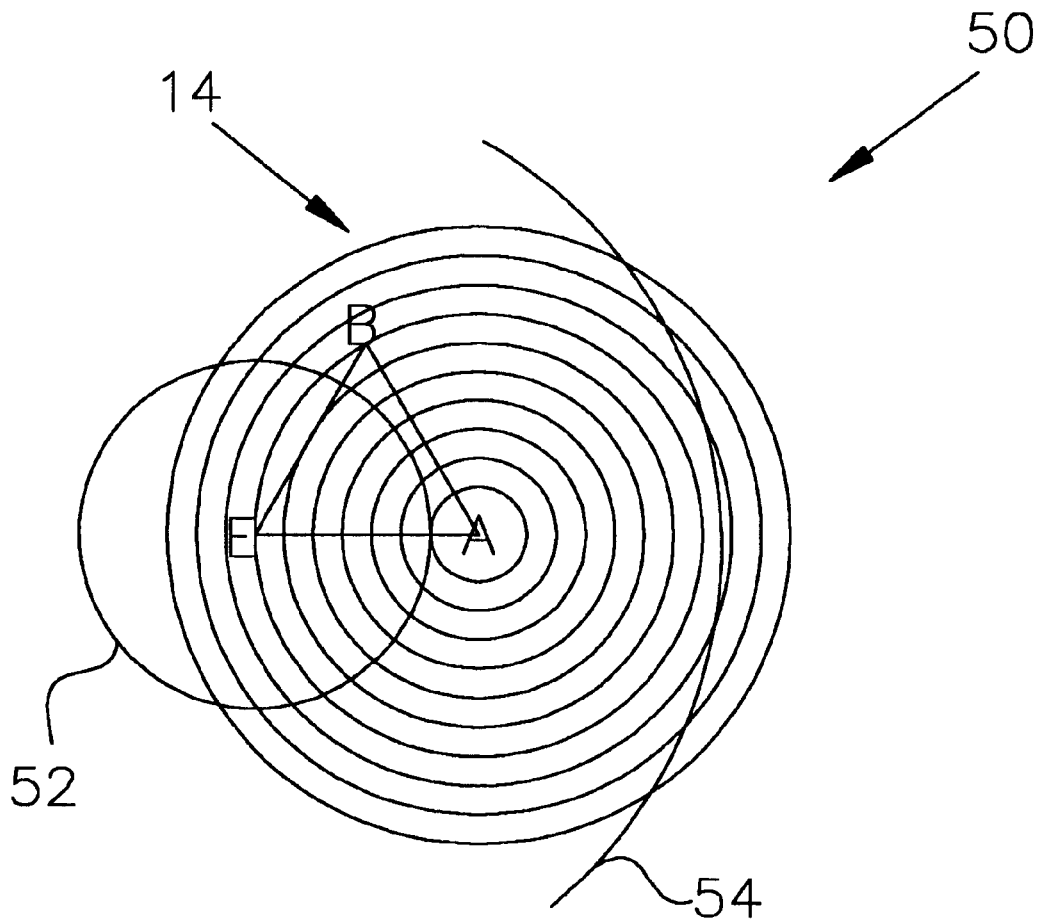
FIG. 3 is an idealized diagram of a reflected concentric ring image observed by the corneal topographer of FIG. 1.

A conventional video camera 44 observes the illuminated cornea along central axis 16. The image is focused on a detector 46 that is coupled to a processor 48, typically in the form of a personal computer. A representative observed image 50 is shown in FIG. 3. Processor 48 determines the shape of the cornea from this image. The rings 14 are represented only by the lines separating them, for clarity. The position of the entrance pupil 52 having a center E on the viewing axis corresponds to fixation of the eye on one of the off-axis (off the central axis) fixation points 34, 36, 38, 40. Point A corresponds to the center of the placido disc image, which is on the central axis. Point B is an arbitrary point on a ring spaced from points A and E, and is used as an example for computation of the curvature of any point on the central zone of the cornea from its approximate center at point E along line BE. Line 54 represents the edge of the cornea, or limbus, which is now also measurable with the method of the present invention.

It is seen that with the fixation point mounted off of the center of the placido target, the eye is correspondingly rotated a known amount of approximately 5–20 degrees off of the central axis and the center of the videokeratograph target, shown as point A, is displaced from the center of the corneal image, shown as point E. The image of the more peripheral rings are thereby positioned over the central cornea. Hence the central region of the cornea is now be measured with respect to a fixed, known peripheral position as shown in FIG. 3. The important region of the cornea that must be measured is that corresponding to the entrance pupil of the eye and is about 3–6 mm in diameter.

In use, the central corneal measurements with respect to point A are transposed to a new reference point that is meaningful with respect to the optics of the eye. The logical position for the new reference point is the center E of the entrance pupil 52. Using a peripheral fixation point 34, 36, 38 or 40 to find reference A, a point B on any ring image in any direction is identified. The power of the cornea at point B is then obtained using the usual methods of videokeratography. A line BE is then defined from point B to the center of the entrance pupil at point E. The power of the cornea at point B is then transposed to the effective power along the axis BE. This method is useful for measuring the central corneal region. A number of sophisticated methods which are not limited to paraxial optics may be used to produce an accurate measurement of the central cornea.

Figure 2:
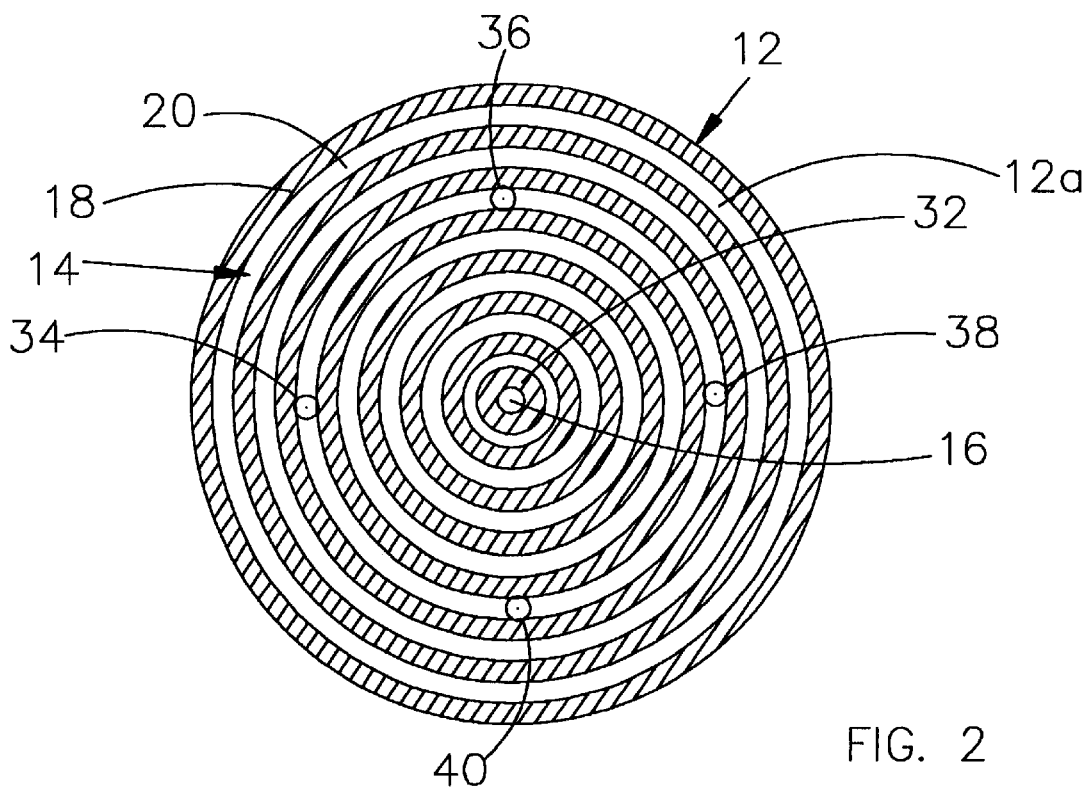
FIG. 2 is a front view of the placido disc of FIG. 1.

The modification of the videokeratograph as provided by the present invention allows a very sensitive and accurate measurement of the central corneal region. If need be, the accuracy can be improved further by repeating the measurement using different fixation points that are mounted on the videokeratograph, as shown in FIGS. 1 and 2. The four fixation points shown, i.e., two in the horizontal (points 34, 38) and two in the vertical (points 36, 40) meridian are adequate for these measurements. However, it may be desirable to use only one, two or three fixation points, or in some cases more than four fixation points.

A target (placido disc) that consists of a multiplicity of fixation points could also be used to align the cornea with the point of greatest curvature (corneal apex) or the line of sight. As an alternative, it may be possible to vary the position of a single fixation point, either using mechanical means or by an optical technique involving a video monitor.

By changing to a peripheral fixation point, it is also found that the videokeratograph rings will now reflect from a peripheral corneal region which includes the corneal limbus 54. However, it is only possible to measure one quadrant of the corneal surface by using this technique. Nevertheless, changing the fixation point to different directions, all of the different regions of the peripheral corneal surface can be measured. Similar techniques, such as is disclosed in U.S. Pat. No. 4,420,228 issued to Humphrey, only give a single measurement at one peripheral point corresponding to each of the peripheral fixations. It does not provide any measurement of the central region as can be accomplished by the present invention.

The present invention is also especially useful in detecting central corneal irregularities, such as central corneal islands and other effects that may result from refractive surgery. It is also useful in determining the true refractive corneal power with respect to the line of sight.

Although the present invention has been described in detail with reference to a particular preferred embodiment, persons possessing ordinary skill in the art to which this invention pertains will appreciate that various modifications and enhancements may be made without departing from the spirit and scope of the claims as written and as judicially construed according to principals of law. The above disclosure is thus intended for purposes of illustration and not limitation.

The invention claimed is:

1. A method of determining a shape of the cornea of an eye, comprising the steps of:

moving at least one of an eye and a placido disc to position the eye on a central axis of the placido disc, wherein a center opening is formed in the placido disc on the central axis;

illuminating the eye with the placido disc;

fixating the eye along a first viewing axis that passes from the eye toward a first fixation point positioned on the placido disc at a location spaced from the center opening;

observing an image of the placido disc reflected from the eye, whereby the central zone of the cornea of the eye reflects an image of a portion of the placido disc spaced from the center opening; and determining from the observed image the shape of at least the central zone of the cornea.

2. A method according to claim 1, further comprising the step of:

changing the relative orientation between the viewing axis and the central axis while maintaining the eye on the central axis; and observing an image of the placido disc reflected from the eye while the viewing axis and central axis are maintained in the changed orientation.

3. A method according to claim 2, wherein said step of changing the orientation comprises fixating the eye along a second viewing axis that passes from the eye toward a second fixation point positioned on the placido disc at a location spaced circumferentially from the first fixation point.

4. A method according to claim 1, further comprising the steps of:

sequentially fixating the eye along a plurality of viewing axes passing from the eye to a corresponding plurality of fixation points located on the placido disc and spaced radially from the central axis and circumferentially around the placido disc;

at each fixation point, observing an image of the placido disc reflected from the eye; and determining from each observed image, at least the shape of a portion of the cornea.

5. The method according to claim 1, further comprising the steps of:
(a) fixating the eye along an additional viewing axis that passes from the eye toward an additional fixation point located on the placido disc at a location spaced from the center opening; and
(b) observing an image of the placido disc reflected from the eye, wherein a central zone of the cornea reflects an image of a portion of the placido disc spaced from the center opening.

6. The method according to claim 5, wherein the determining step comprises determining the shape of the central zone of the cornea from images observed when the eye was fixated along the first and the additional viewing axes.

7. The method according to claim 5, further comprising the step of repeating steps (a)–(b) a plurality of times.

8. The method according to claim 5, further comprising a step of determining a shape of a peripheral portion of the cornea based on images observed when the eye was fixated along the first and the additional viewing axes.

9. The method according to claim 1, further comprising a step of determining a shape of a peripheral portion of the cornea based on the image observed when the eye was fixated along the first viewing axis.

10. A corneal topographer, comprising:
a target having a center positioned on a central axis and at least one fixation point positioned on the target at a location spaced from the center such that a central zone of a cornea of an eye positioned at an observation station and located on the central axis and fixated on said at least one fixation point will reflect an image of a portion of the target spaced from the center;
a detector positioned to detect an image of said target reflected from the cornea of an eye positioned at the observation station; and
a processor configured to determine a shape of at least the central zone of the cornea based on the detected image.

11. A corneal topographer according to claim 10, further having a plurality of fixation points distributed around the center of said target.

12. The corneal topographer according to claim 10, wherein the processor is also configured to determine a shape of a peripheral portion of the cornea based on the detected image.

13. The corneal topographer according to claim 10, further comprising a memory device for storing a plurality of detected images, and wherein the processor is configured to determine the shape of at least the central portion of the cornea based on a plurality of detected images.

14. The corneal topographer according to claim 13, wherein the processor is configured to determine a shape of a plurality of peripheral portions of the cornea based on a plurality of detected images.

15. The corneal topographer according to claim 10, wherein the target is configured such that the central zone of an eye positioned at an observation station located on the central axis will reflect an image of a portion of the target spaced from the center, substantially along the central axis.

16. The corneal topographer according to claim 10, wherein a central opening is formed on the target along the central axis.

17. The corneal topographer according to claim 16, wherein the detector is configured to detect an image of the target reflected from an eye and through the central opening.

18. The corneal topographer according to claim 10, wherein the target comprises a placido disc having a pattern thereon.

19. The corneal topographer of claim 18, wherein the pattern of the placido disc comprises a plurality of alternating light and dark concentric rings.

20. A corneal topographer, comprising:
means for projecting a test image onto a cornea of an eye when the eye is located at an observation station and is oriented along a central axis;
means for fixating the eye along at least one fixation axis which passes from the eye to a fixation point that is spaced from the central axis;
means for detecting a portion of the test image reflected from the cornea of the eye while the eye is fixated along the at least one fixation axis; and
means for determining a shape of at least a central region of the cornea of the eye based on the detected reflected test image.

21. The corneal topographer of claim 20, wherein the detecting means detects a portion of the test image reflected from the central region of the cornea of the eye.

22. The corneal topographer of claim 20, wherein the shape determining means also determines a shape of at least one peripheral portion of the cornea of the eye based on a portion of the test image reflected from a peripheral portion of the cornea of the eye.

23. The corneal topographer of claim 20, further comprising means for storing a plurality of detected reflected test images, and wherein the determining means determines a shape of the cornea of the eye based on a plurality of detected reflected test images.

24. The corneal topographer of claim 20, wherein the fixating means comprises means for fixating the eye along a plurality of fixation axes passing from the eye to a corresponding plurality of fixation points spaced from the central axis.

* * * * *